United States Patent [19]

Nabatame

[11] Patent Number: 5,740,225
[45] Date of Patent: Apr. 14, 1998

[54] RADIATION THERAPY PLANNING METHOD AND ITS SYSTEM AND APPARATUS

[75] Inventor: Takeo Nabatame, Tochigi, Japan

[73] Assignee: Kabushiki Kaisha Toshiba, Kawasaki, Japan

[21] Appl. No.: 761,141

[22] Filed: Dec. 6, 1996

[30] Foreign Application Priority Data

Dec. 7, 1995 [JP] Japan ................................. 7-318706

[51] Int. Cl.$^6$ ............................................. A61N 5/10
[52] U.S. Cl. ................................... 378/65; 378/901
[58] Field of Search ............................ 378/65, 901

[56] References Cited

U.S. PATENT DOCUMENTS

| | | | |
|---|---|---|---|
| 5,513,238 | 4/1996 | Leber et al. | 378/65 |
| 5,526,395 | 6/1996 | Van De Geijn et al. | 378/64 |
| 5,602,892 | 2/1997 | Llacer | 378/65 |

FOREIGN PATENT DOCUMENTS 4-84942   3/1992   Japan .

OTHER PUBLICATIONS

Hiroyuki Fujikawa, et al. "Acuracy of Radiotherapy Treatment Planning Using CT–Scanogram", Japanese Journal of Radiological Technology, vol. 51, No. 3, (p. 269), Mar. 1, 1995.

*Primary Examiner*—David P. Porta
*Assistant Examiner*—David Vernon Bruce
*Attorney, Agent, or Firm*—Oblon, Spivak, McClelland, Maier & Neustadt, P.C.

[57] ABSTRACT

A plurality of axial images covering a region of interest in a subject to be treated are scanned and voxel data of the subject are produced from the axial images. The provisional location of an isocenter and the direction of radiation are determined over the axial images. A DRR of the subject viewed from the source of radiation is developed in accordance with the provisional isocenter location, the radiating direction, and the distance between the isocenter and the radiation source. The DRR is displayed together with three cross section images which represent an isocenter plane including the isocenter and arranged vertical to a line extending between the isocenter and the radiation source, a gantry rotation plane including the isocenter, and a plane including the isocenter and arranged vertical to both the isocenter plane and the gantry rotation plane. Each of the three cross section images indicates cross-hair ROI representing the other two planes and a cross-hair ROI representing the direction of radiation. The field of radiation is then determined over the three cross section images or the DRRs. The three cross section images and the DRRs can be updated in response to shift and rotation of the cross-hair ROIs.

12 Claims, 6 Drawing Sheets

I/C PLANE
(OBLIQUE IMAGE)

GANTRY ROTATION PLANE

PLANE VERTICAL
TO THE OTHER
TWO PLANES

TRANSLUCENT IMAGE

RADIATION THERAPY PLANNING METHOD AND ITS SYSTEM AND APPARATUS

BACKGROUND OF THE INVENTION

1. Field of the Invention

The present invention relates to a radiation therapy planning method and its system and apparatus, and more particularly to a radiation therapy planning method which accurately determines an isocenter and a radiation field with the use of a digitally reconstructed radiograph (DRR) or translucent image, a system and its apparatus.

2. Description of the Related Art

Such radiotherapy treatments for particular cancers are widely known using beams of X-ray or electron emitted from a linear accelerator (referred to as a linac hereinafter). Alternatively, microtron or betatron beams produced by the acceleration of electron different from the linac technique are used for the radiotherapy treatment. Recently, a variety of large-scale radiotherapy particle accelerators have been developed and available.

An improved radiation therapy planning is then requested for providing the energy of radiation in a spatially and timely optimum profile so that a higher dose is directed to the target region to be treated while lower, acceptable doses fall on its surrounding normal organs causing no serious injury.

In the radiotherapy treatment with external radiation of radioactive beams such as X-ray or electron over a patient, it is noted that the profile of the radiation is varied depending on the size and quality of the patient body and the shape and location of an affected part or organ.

Accordingly, any radiation therapy planning has to be carefully designed in view of the clinical history and individuality of the patient.

Conventional radiation therapy plannings employ a technique of X-ray simulation for defining the position of a patient relative to the X-ray source which is geometrically equivalent to the location of the patient relative to the radiation source in a radiation treatment apparatus. The X-ray simulation is realized by a mechanism (of an X-ray simulator) capable of controlling the geometrical parameters such as the distance between a radiation source and the rotation center of a clinical bed and the beam limiter aperture which are compatible with those of a radiation treatment apparatus shown in FIG. 6. For identifying the location, shape, and size of a part to be treated and determining the parameters for radiation such as the angle and field of radiation, X-ray images or radiographs are produced by the X-ray simulator. The part to be treated is projected and recorded together with a grating of wire collimator lines and a scale of simulation onto a the X-ray film. The data from the X-ray radiographs are then examined to locate and mark down the patient.

The X-ray simulator of a known type is incapable of measuring a depth, as the result, it produces only two-dimensional images. This will decline the accuracy of tumor identification and fail to develop an advanced scheme for the radiation treatment.

For compensation, there are introduced other types of simulation in which the three-dimensional data (voxel data) of a subject is produced with an X-ray CT apparatus and used for simulating a three-dimensional model. Among such types of simulation are a scano plan and an oblique plan for radiation therapy.

The scano plan is relatively a simple method using both scano and axial images. The axial images and the scano image viewed from the direction of radiation are produced by an X-ray CT scanner and the field of radiation is directly determined over the scano image. The location of an isocenter which is a cross point between the gantry rotation axis e and the beam limiter rotation axis d of the radiation treatment apparatus and will be referred to as an I/C hereinafter is identified from a combination of the scano and axial images. The scano plan permits the axial images to be overlapped by a beam profile of radiation for estimating the radiation therapy planning.

The oblique plan is for determining an object to be irradiated over the axial images. More specifically, each slice of the axial images produced by an X-ray CT scanner is examined to identify tumors to be treated and organs to be protected from radiation, and the I/C and the angle of radiation are determined to define the field of radiation automatically. The oblique plan allows multiple field irradiation in which beams of radiation are directed from different angles, arc therapy radiation in which radiation is made at a variable angle, and conformal therapy in which both the angle of radiation and the size of beam limiter aperture are varied. Through determining the radiation therapy planning with reference to the axial and oblique images, a translucent image geometrically equivalent to the radiograph viewed from the direction of radiation can be developed. This DRR is however a result of the planning and may be effective for reviewing the planning but not useful for estimating the planning because the planning is hardly modified while monitoring the DRR.

In the scano plan type of conventional radiation therapy planning, the scano image are produced with the use of a parallel beam and geometrically different from the DRR of a subject produced by a fan beam from the source of radiation and may have a degree of distortion. This will impair the accuracy of simulation and prevent the planning from having a desired angle of radiation and being executed with ease.

The oblique plan type of conventional radiation therapy planning requires entry of target data over a considerable number of the axial images, hence giving complications of the target setting and an increased length of the operating time.

SUMMARY OF THE INVENTION

It is an object of the present invention, in view of the above aspects, to provide a radiation therapy planning method capable of determining a desired angle of radiation within a shorter period of time, and a system and its apparatus employing the method.

It is another object of the present invention to provide a radiation therapy planning method capable of determining the location of an I/C and the angle of radiation by a manner similar to a common X-ray simulation technique without holding the patient to an X-ray simulator for a longer, painful duration, and a system and its apparatus employing the method.

It is a further object of the present invention to provide a radiation therapy planning method capable of minimizing entry operation and reducing labor of the operator, and a system and its apparatus employing the method.

For achievement of the above object, there is provided a radiation therapy planning method of estimating the direction of radiation and/or the field of radiation prior to actual radiation treatment, comprising the steps of: producing voxel data of a region of interest in a subject to be treated; constructing a translucent image of the subject from the voxel data which is viewed from a desired location or direction; and determining the field of radiation over the translucent image.

Also, there is provided a radiation therapy planning method of estimating the direction of radiation and/or the field of radiation prior to actual radiation treatment, comprising the steps of: shooting a plurality of axial images covering a region of interest in a subject to be treated; producing voxel data of the subject from the axial images; determining the provisional location of an isocenter and the direction of radiation over the axial images; developing a translucent image of the subject, which is viewed from the source of radiation, in accordance with the provisional location of the isocenter, the direction of radiation, and the distance between the isocenter and the radiation source over the axial images; displaying the translucent image together with three images which represent an isocenter plane including the isocenter and arranged vertical to a line between the isocenter and the radiation source, a gantry rotation plane including the isocenter, and a plane including the isocenter and arranged vertical to both the isocenter plane and the gantry rotation plane; indicating in each of the three plane images a cross-hair ROI representing the location of the other two planes and a cross-hair ROI representing the direction of radiation; determining the field of radiation over the three plane images or the translucent image; shifting and/or rotating the ROIs; and updating at real time the three plane images and the translucent image in response to the shift and rotation of the ROIs.

Furthermore, there is provided a radiation therapy planning method of estimating the direction of radiation and/or the field of radiation prior to actual radiation treatment, comprising the steps of: shooting a plurality of axial images covering a region of interest in a subject to be treated; producing voxel data of the subject from the axial images; determining the provisional location of an isocenter and the direction of radiation over the axial images; developing a translucent of the subject, which is viewed from the source of radiation, in accordance with the provisional location of the isocenter, the direction of radiation, and the distance between the isocenter and the radiation source over the axial images; displaying the translucent image together with three images which represent a gantry rotation plane, a coronal plane, and a sagittal plane all including the isocenter; indicating in each of the three plane images a cross-hair ROI representing the location of the other two planes and a cross-hair ROI representing the direction of radiation; determining the field of radiation over the three plane images or the translucent image; shifting and/or rotating the ROIs; and updating at real time the three plane images and the translucent image in response to the shift and rotation of the ROIs.

For achievement of the above object, there is provided a radiation therapy planning apparatus comprising: a voxel data producing means for producing voxel data of a region of interest in a subject to be treated from a plurality of axial images received; a cross section image reconstructing means for reconstructing a group of selected cross section images from the voxel data; and a translucent image developing means for developing a translucent image of the subject viewed from the direction of radiation which is predetermined.

Also, there is provided a radiation therapy planning system comprising: an X-ray CT scanner for producing a plurality of axial images covering a region of interest in a subject to be treated; a radiation therapy planning apparatus for producing voxel data of the subject from the axial images, reconstructing a selected number of cross section images according to the location of an isocenter and the angle of radiation entered, and developing a translucent image of the subject viewed from the source of radiation in accordance with the isocenter location, the radiation angle, and the distance between the isocenter and the radiation source; a display means for displaying the axial images as well as the cross section images and the translucent image produced by the radiation therapy planning apparatus; an entry means for determining the isocenter location and the radiation angle over the axial images displayed on the display means and the radiation field over the translucent image displayed on the display means, and if it is desired to modify the translucent image, changing the isocenter location and the radiation angle over the cross section images displayed on the display means; and a projector means responsive to data of the isocenter location from the radiation therapy planning apparatus for projecting a laser marking of the isocenter onto the body surface of the subject.

A preferred embodiment of the present invention may further comprises an external memory means for saving the relevant data for radiation therapy planning.

In another preferred embodiment of the present invention, the cross section images represent three planes: an isocenter plane including the isocenter and arranged vertical to a line extending between the isocenter and the radiation source, a gantry rotation plane including the isocenter, and a plane including the isocenter and arranged vertical to both the isocenter plane and the gantry rotation plane.

In a further preferred embodiment of the present invention, the image of each of the three planes indicates the other two planes with a cross-hair ROI.

In a still further preferred embodiment of the present invention, the cross-hair ROI is shifted or rotated by the entry means to change the isocenter location and the radiation angle.

In a still further preferred embodiment of the present invention, the cross section images and the translucent image displayed on the display means are updated at real time in response to the shift and rotation of the cross-hair ROI.

In a sill further preferred embodiment of the present invention, the display means indicates overlapping of a beam profile of radiation with the axial images and both BE and BP planes after the isocenter location, radiation angle, and radiation field are determined.

In a still further preferred embodiment of the present invention, the cross section images represent three planes: a gantry rotation plane, a coronal plane, and a sagittal plane all including the isocenter.

The nature, principle and utility of the invention will become more apparent from the following detailed description when read in conjunction with the accompanying drawings.

DESCRIPTION OF THE PREFERRED EMBODIMENTS

Embodiments of the present invention will be described in more details referring to the accompanying drawings.

Figure 2:
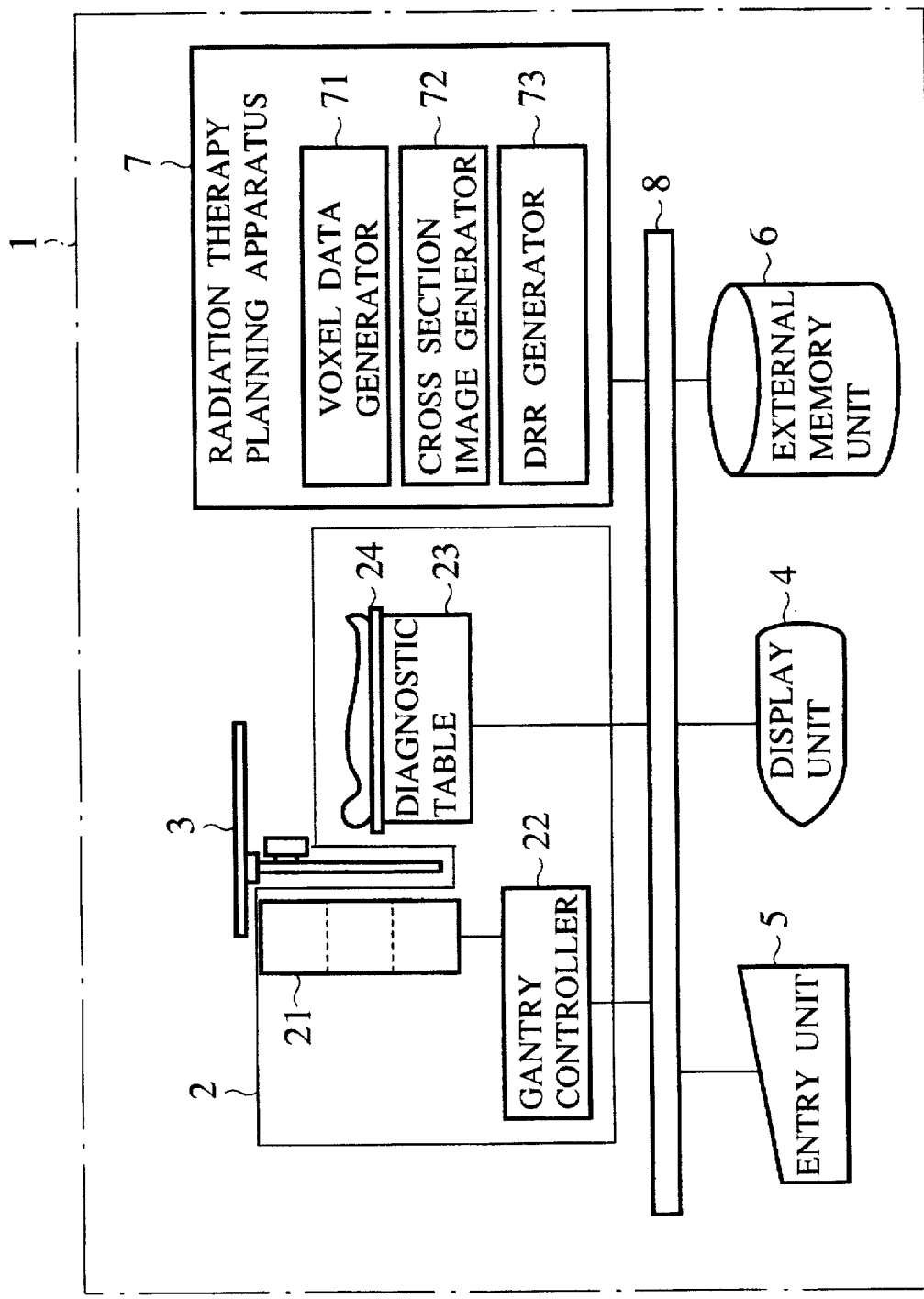
FIG. 2 is a block diagram showing schematically a radiation therapy planning system of the present invention.

A radiation therapy planning system according to the present invention is explained as shown in FIG. 2. The radiation therapy planning system 1 comprises an X-ray CT unit 2, a projector unit 3, a display unit 4, an entry unit 5, an external memory unit 6, a radiation therapy planning apparatus 7, and a bus 8 connecting the units to each other.

The X-ray CT unit 2 is well known as provided for shooting a succession of axial images of slices to gain the voxel data b of a subject to be treated. A gantry 21 of the X-ray CT unit 2 contains an X-ray tube and an X-ray detector located opposite to each other and on both sides of a center opening and is driven for rotation about the opening by a gantry controller 22. A tabletop 24 of a diagnostic table 23 on which the subject to be scanned is positioned is moved in and from the opening of the gantry 21.

The diagnostic table 23 includes a drive mechanism for moving the tabletop 24 longitudinally. A combination of the rotation of the gantry 21 and the longitudinal movement of the tabletop 24 permits the X-ray CT unit 2 to helically scan the subject on the tabletop 24 and produce a succession of axial images within a short duration of time.

The projector unit 3 projects a profile of the I/C and defines the field of radiation over the surface of the subject positioned on the tabletop 24.

The display unit 4 displays the axial images of the subject; images on the I/C plane, images on the gantry rotation plane, images perpendicular to both the I/C and gantry rotation planes, X-ray images, etc.

The entry unit 5 includes a pointing device such as a mouse or a tracking ball for entry of relevant parameters such as the location of the I/C and the angle of radiation by pointing locations on a display of the display unit 4.

The radiation therapy planning apparatus 7 comprises a voxel data b generating unit 71 for producing the voxel data b of the subject from a succession of the axial sliced images taken by the X-ray CT unit 2, a cross section image reconstructing unit 72 for reconstructing images of selected cross sections from the voxel data b, a DRR developing unit 73 for developing DRR of the subject viewed from a predetermined direction of radiation. The radiation therapy planning apparatus 7 is adapted for displaying a given number of reconstructed images on the display unit 4 and transmitting desired data to and from the external memory unit 6.

Figure 1:
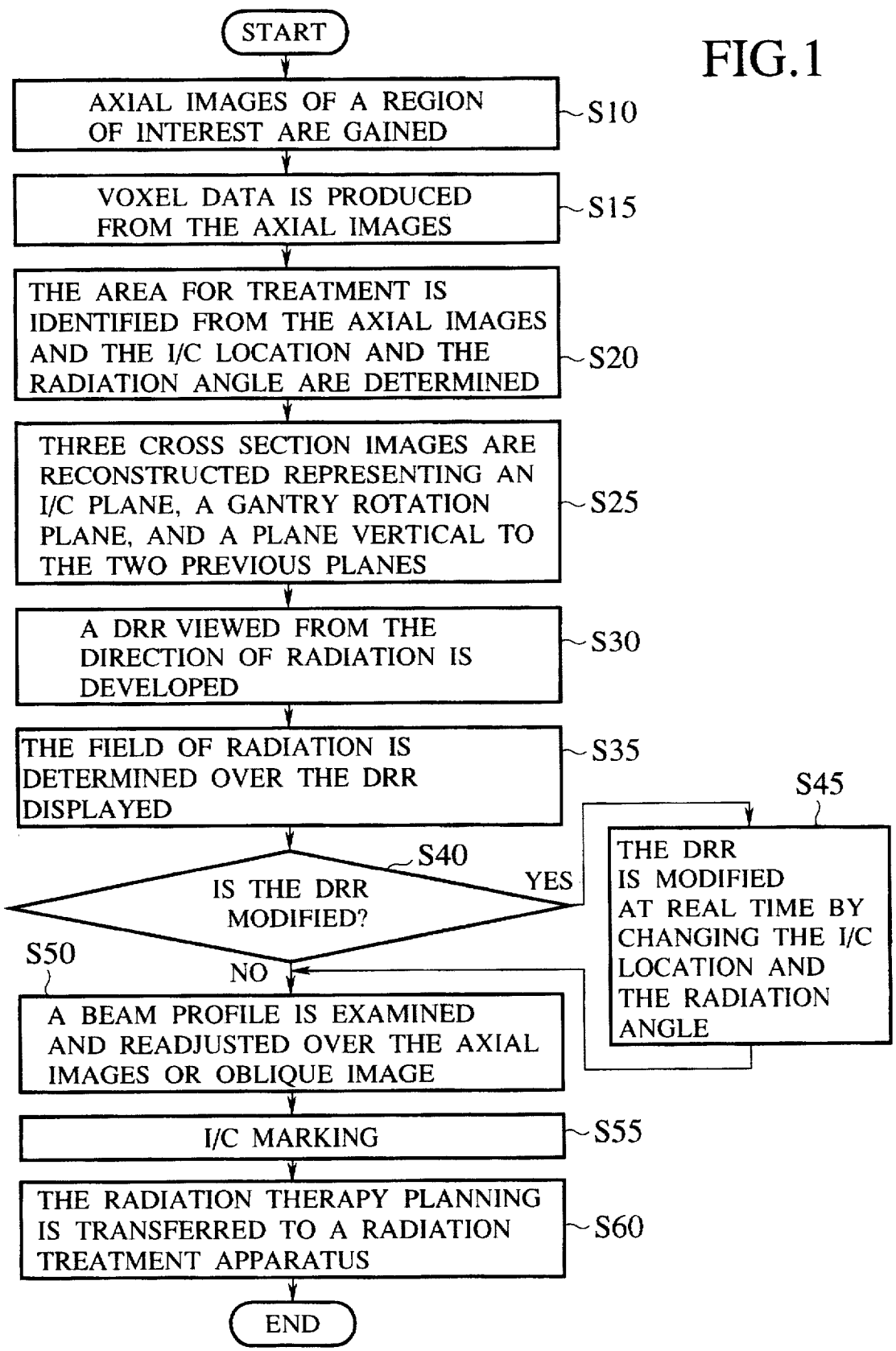
FIG. 1 is a flowchart showing steps of a radiation therapy planning method of the present invention.

A procedure of the radiation therapy planning method of the present invention will now be explained referring to a flowchart of FIG. 1. The procedure starts with the X-ray CT unit 2 producing a succession of the axial images representing a region of interest on the subject (Step S10). The voxel data b or three-dimensional volume data is then constructed from the axial images by a common interpolation technique (Step S15).

This is followed by viewing selected ones of the axial images saved and displayed in an order of the sliced locations, identifying the location of tumors, and determining the provisional location of the I/C and the angle of radiation (Step S20). It is also a good idea for ease of the setting to display the I/C location and the radiation angle in combination with a beam profile which is variable in divergence. In general, the I/C may be located either on the axis of the subject body or on the center of a part to be treated.

As the provisional location of the I/C and the angle of radiation have been determined to locate the subject relative to the source of radiation, the images of three cross sections of the subject taken along the I/C plane, the gantry rotation plane, and the plane perpendicular to the two previous planes all including the I/C are reconstructed from their voxel data b and displayed together on the display unit 4 (Step S25). Each of the three images includes a cross-hair ROI representing the other two planes.

Figure 3B:
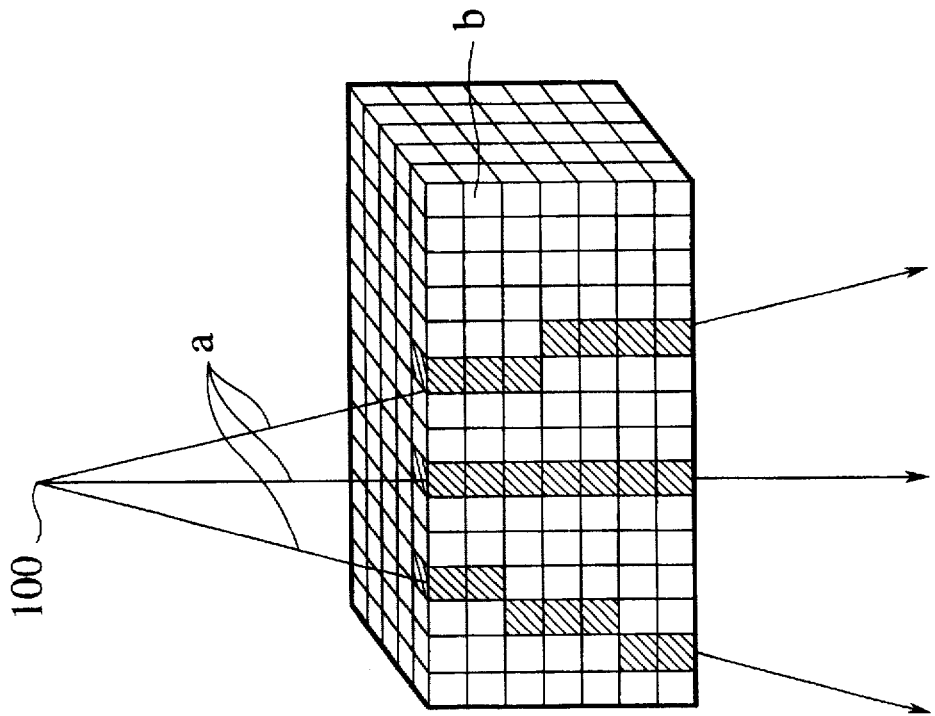
FIGS. 3A and 3B are diagrams illustrating an isocenter plane and explaining production of DRR from voxel data.
Figure 3A:
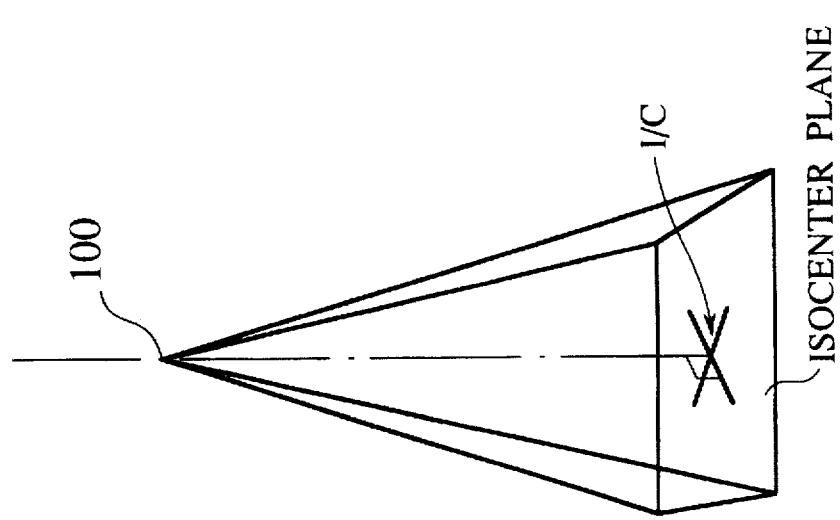

The I/C plane is a plane vertical to a line between the I/C and the radiation source 100 as shown in FIG. 3A. When the I/C is present on the axis of the subject body, the image on the I/C plane is a coronal image but otherwise, a common oblique image.

The location of the radiation source 100 is then calculated from the I/C location, the radiation angle, and the distance between the I/C and the radiation source 100 predetermined and saved, and the DRR of the voxel data b is determined with the view point aligned to the radiation source 100 (Step S30). As shown in FIG. 3B, the DRR is calculated using a maximum and a sum average of CT values of the voxel data b fallen on a plurality of beam paths a extending from the radiation source 100 to the DRR developing plane.

Figure 4:
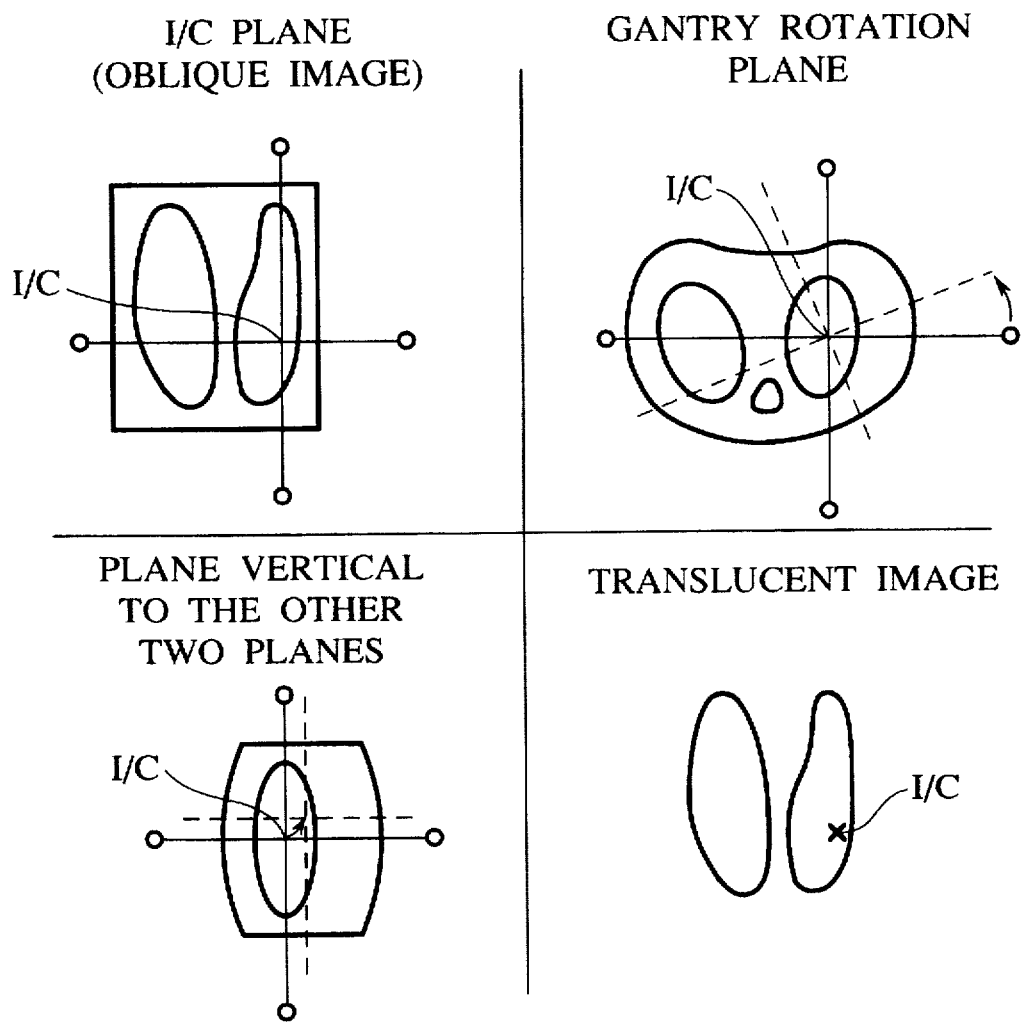
FIG. 4 is a view of a screen display produced in the radiation therapy planning system.

This is followed by displaying the DRR on the display unit 4 and determining the field of radiation with the entry unit 5 (Step S35). Simultaneously, the cross sections of the subject produced in relation to the prescribed three planes at Step S25 are displayed together with the DRR on the display unit 4, as shown in FIG. 4.

When it is desired to modify the DRR (as judged "yes" at Step S40), desired parameters of the I/C location and the radiation angle are entered through the entry unit 5. More particularly, the I/C location and the radiation angle are changed by shifting and rotating the cross-hair ROI. In response to the shift and rotation of the cross-hair ROI, the radiation therapy planning apparatus 7 updates the DRR and the three cross section images at real time and indicates them on the display unit 4 (Step S45).

In updating the DRR and the three cross section images, the duration from commanding the shift and rotation of the cross-hair ROI to the display of the updated images is minimized by increasing the pixel pitch of the images to be reconstructed and thus decreasing the size of calculation. If required, the images with a higher resolution are calculated and displayed. This will improve the efficiency of operation.

When the I/C location and the radiation angle have been determined and the DRR is produced, the field of radiation may be modified.

Figure 5B:
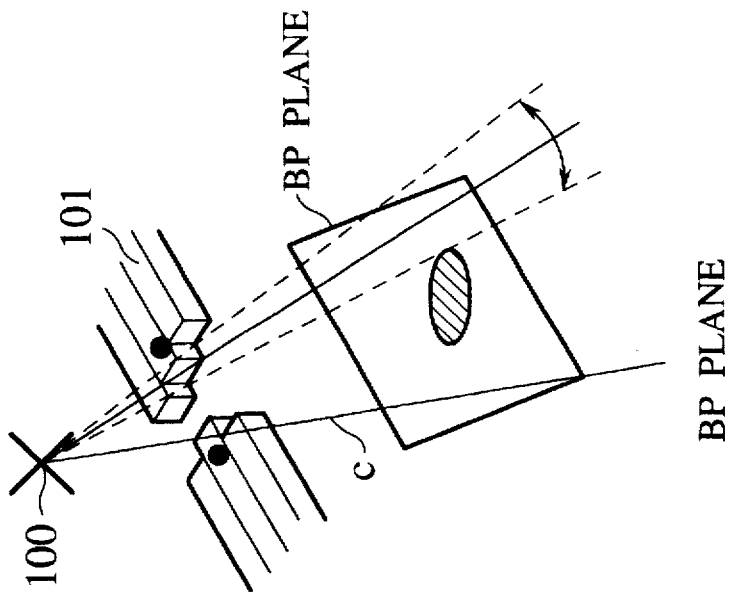
FIG. 5 is a diagram explaining configurations of the field of radiation across BE and BP planes.
Figure 5A:
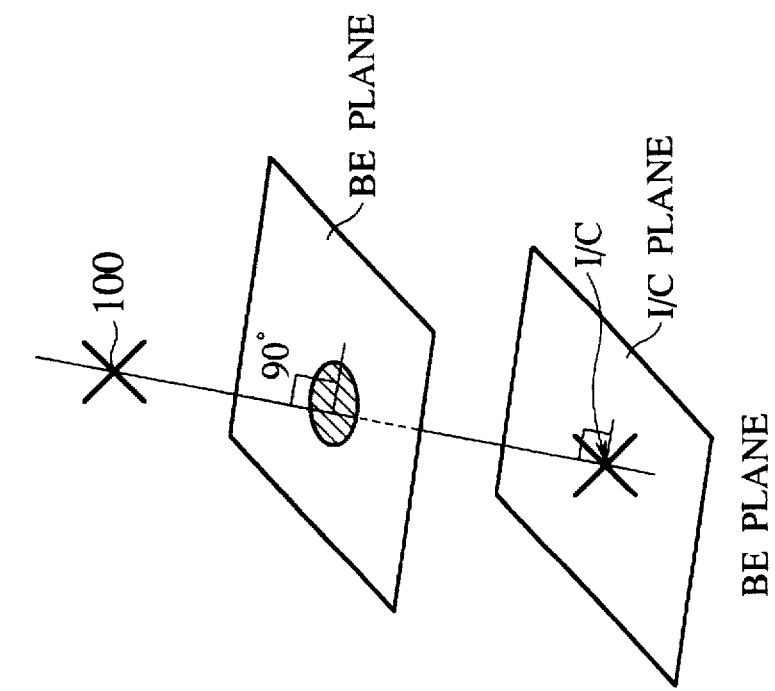
Figure 6:
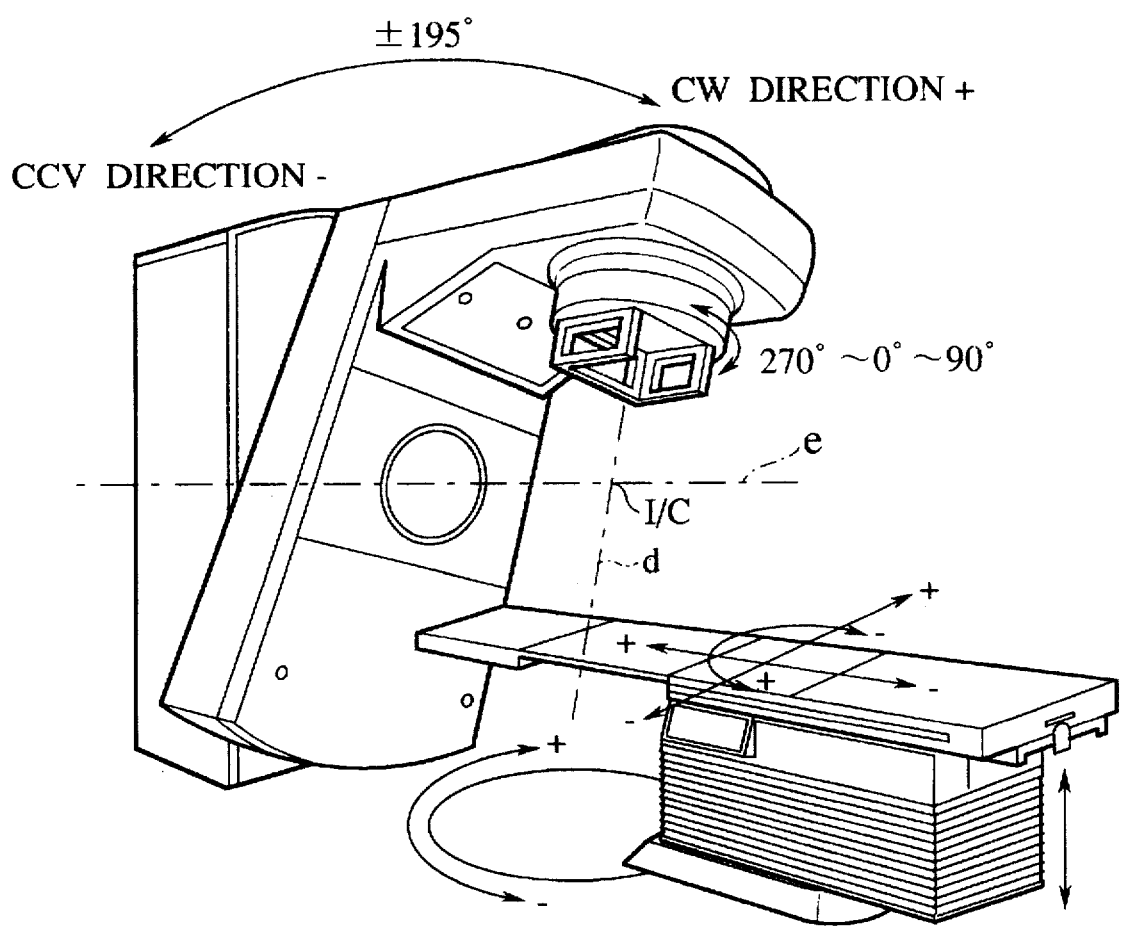
FIG. 6 is a perspective outside view of a common radiotherapy treatment apparatus with its related coordinates.

In particular, after the I/C location, the radiation angle, and the radiation field are determined, any of the axial images, the beam profile configuration across BE (beam's eyes) plane or BP (beam path) plane, or the radiation field may be reviewed and readjusted as desired as shown in FIGS. 5A and 5B (Step S50). The BE plane is an oblique plane extending in parallel with the I/C plane and the radiation field is enlarged or reduced in size depending on the distance between the radiation source 100 and the oblique plane.

The BP plane is an oblique plane including the radiation source 100 and thus determining a beam profile c for the radiation treatment. In case of a multi-division aperture control such as a multi-leaf collimator 101, the BP plane is utilized for finely adjusting the beam profile c with a cross section defined thereon by a combination of the radiation source 100 and the aperture control.

Upon the review and adjustment of the beam profile c being completed, the data of the I/C location is transmitted from the radiation therapy planning apparatus 7 to the projector unit 3 where it is used as a reference for the positioning in the radiation treatment. More specifically, the I/C is projected in the form of a laser mark by the projector unit 3 on the surface of the subject body. The laser mark is then traced with a marking pen or the like for I/C marking (Step S55). The data may be recorded on a film or transferred directly to a radiation treatment apparatus for controlling the radiation (Step S60).

Although the prescribed embodiment permits a group of the I/C plane, the gantry rotation plane including the I/C, the plane arranged perpendicular to the I/C plane and the gantry rotation plane and including the I/C to be displayed on the display unit 4, the gantry rotation plane including the I/C will be displayed in combination with a coronal plane and a sagittal plane both including the I/C.

As set forth above, the present invention is advantaged by planning the radiation treatment with a desired angle of radiation within a shorter period of time.

Also, the present invention allows the I/C location and the radiation angle to be determined by a sophisticated manner similar to a known technique of X-ray simulation, hence minimizing the involving time of a patient and easing the pain of binding.

Furthermore, the present invention permits the operator to enter a far less number of parameters for the radiotherapy planning with a minimum of complications.

It should be understood that many modifications and adaptations of the invention will become apparent to those skilled in the art and it is intended to encompass such obvious modifications and changes in the scope of the claims appended hereto.

What is claimed is:

1. A radiation therapy planning method of estimating the direction of radiation and/or the field of radiation prior to actual radiation treatment, comprising the steps of:

producing voxel data of a region of interest in a subject to be treated;

constructing a translucent image of the subject from the voxel data which is viewed from a desired location or direction; and determining the field of radiation over the translucent image.

2. A radiation therapy planning method of estimating the direction of radiation and/or the field of radiation prior to actual radiation treatment, comprising the steps of:

shooting a plurality of axial images covering a region of interest in a subject to be treated;

producing voxel data of the subject from the axial images:

determining a provisional location of an isocenter and the direction of radiation over the axial images;

developing a translucent image of the subject, which is viewed from a source of radiation, in accordance with the provisional location of the isocenter, the direction of radiation, and the distance between the isocenter and the radiation source over the axial images;

displaying the translucent image together with three images which represent an isocenter plane including the isocenter and arranged vertical to a line between the isocenter and the radiation source, a gantry rotation plane including the isocenter, and a plane including the isocenter and arranged vertical to both the isocenter plane and the gantry rotation plane;

indicating in each of the three plane images a cross-hair ROI representing the location of the other two planes and a cross-hair ROI representing the direction of radiation;

determining the field of radiation over the three plane images or the translucent image;

shifting and/or rotating the ROIs; and updating at real time the three plane images and the translucent image in response to the shift and rotation of the ROIs.

3. A radiation therapy planning method of estimating the direction of radiation and/or the field of radiation prior to actual radiation treatment, comprising the steps of:

shooting a plurality of axial images covering a region of interest in a subject to be treated;

producing voxel data of the subject from the axial images:

determining a provisional location of an isocenter and the direction of radiation over the axial images;

developing a translucent image of the subject, which is viewed from a source of radiation, in accordance with the provisional location of the isocenter, the direction of radiation, and the distance between the isocenter and the radiation source over the axial images;

displaying the translucent image together with three images which represent a gantry rotation plane, a coronal plane, and a sagittal plane all including the isocenter;

indicating in each of the three plane images a cross-hair ROI representing the location of the other two planes and a cross-hair ROI representing the direction of radiation;

determining the field of radiation over the three plane images or the translucent image;

shifting and/or rotating the ROIs; and updating at real time the three plane images and the translucent image in response to the shift and rotation of the ROIs.

4. A radiation therapy planning apparatus comprising:

a voxel data producing means for producing voxel data of a region of interest in a subject to be treated from a plurality of axial images received;

a cross section image reconstructing meads for reconstructing a group of selected cross section images from the voxel data; and a translucent image developing means for developing a translucent image of the subject viewed from a predetermined direction of radiation.

5. A radiation therapy planning system comprising:

an X-ray CT scanner for producing a plurality of axial images covering a region of interest in a subject to be treated;

a radiation therapy planning apparatus for producing voxel data of the subject from the axial images, reconstructing a selected number of cross section images according to the location of an isocenter and an angle of radiation entered, and developing a translucent image of the subject viewed from a source of radiation in accordance with the isocenter location, the radiation angle, and the distance between the isocenter and the radiation source;

a display means for displaying the axial images as well as the cross section images and the translucent image produced by the radiation therapy planning apparatus;

an entry means for determining the isocenter location and the radiation angle over the axial images displayed on the display means and the radiation field over the translucent image displayed on the display means, and if it is desired to modify the translucent image, changing the isocenter location and the radiation angle over the cross section images displayed on the display means; and a projector means responsive to data of the isocenter location from the radiation therapy planning apparatus for projecting a laser marking of the isocenter onto the body surface of the subject.

6. A radiation therapy planning system according to claim 5, further comprising an external memory means for saving the relevant data for radiation therapy planning.

7. A radiation therapy planning system according to claim 5, wherein the cross section images represent the planes: an isocenter plane including the isocenter and arranged vertical to a line extending between the isocenter and the radiation source, a gantry rotation plane including the isocenter, and a plane including the isocenter and arranged vertical to both the isocenter plane and the gantry rotation plane.

8. A radiation therapy planning system according to claim 7, wherein the image of each of the three planes indicates the other two planes with a cross-hair ROI.

9. A radiation therapy planning system according to claim 8, wherein the cross-hair ROI is shifted or rotated by the entry means to change the isocenter location and the radiation angle.

10. A radiation therapy planning system according to claim 9, wherein the cross section images and the translucent image displayed on the display means are updated at real time in response to the shift and rotation of the cross-hair ROI.

11. A radiation therapy planning system according to claim 5, wherein the display means indicates overlapping of a beam profile of radiation with the axial images and both BE and BP planes after the isocenter location, radiation angle, and radiation field are determined.

12. A radiation therapy planning system according to claim 5, wherein the cross section images represent three planes: a gantry rotation plane, a coronal plane, and a sagittal plane all including the isocenter.

* * * * *